United States Patent
Wagner et al.

[11] Patent Number: 6,081,127
[45] Date of Patent: Jun. 27, 2000

[54] METHOD AND ARRANGEMENT FOR THE RESPONSE ANALYSIS OF SEMICONDUCTOR MATERIALS WITH OPTICAL EXCITATION

[75] Inventors: Matthias Wagner; Hans-Dieter Geiler, both of Jena, Germany

[73] Assignee: Leica Microsystems Wetzlar GmbH, Wetzlar, Germany

[21] Appl. No.: 08/615,427

[22] Filed: Mar. 14, 1996

[30] Foreign Application Priority Data

Mar. 31, 1995 [DE] Germany .................. 195 11 869

[51] Int. Cl.$^7$ .................. G01R 31/28; G01R 31/308
[52] U.S. Cl. .................. 324/765; 324/752
[58] Field of Search .................. 324/501, 751, 324/752, 753, 765, 766, 767

[56] References Cited

U.S. PATENT DOCUMENTS

| | | | |
|---|---|---|---|
| 4,122,383 | 10/1978 | von Roos | 324/752 |
| 4,661,770 | 4/1987 | von Roos | 324/767 |
| 5,237,266 | 8/1993 | Endreidi et al. | 324/767 |
| 5,302,832 | 4/1994 | Kitagawara et al. | 250/459.1 |
| 5,408,327 | 4/1995 | Geiler et al. | 356/432 |
| 5,490,090 | 2/1996 | Ellis | 324/501 |

FOREIGN PATENT DOCUMENTS

| | | |
|---|---|---|
| 05 45523A2 | 6/1993 | European Pat. Off. . |
| 40 35266A1 | 5/1992 | Germany . |
| 42 17 097 A1 | 11/1993 | Germany . |
| 42 23337A1 | 1/1994 | Germany . |

OTHER PUBLICATIONS

M. Wagner and H.D. Geiler; Single–beam Thermowave Analysis of Ion Implanted and Laser annealed semiconductors; Nov. 1991; pp. 1088–1093.

"Optical Phase Shift Measurement of Carrier Decay–Time on Thin Semiconductor Samples with Surface Losses," *Solid–State Electronics,* H.R. Zwicker et al., vol. 14, 1971, (month unavailable) pp. 1023–1033.

*Primary Examiner*—Ernest Karlsen
*Attorney, Agent, or Firm*—McAulay Nissen Goldberg & Kiel, LLP

[57] ABSTRACT

The invention is directed to a method and an arrangement for the response analysis of semiconductor materials with optical excitation. The object of the invention, to find a new type of response analysis of semiconductor materials with optical excitation which also allows a sufficiently precise detection of the charge carrier wave with a higher excitation output and a shorter charge carrier lifetime, is met according to the invention in that an exciting laser beam is intensity-modulated with two discrete modulation frequencies ($\Omega_1$; $\Omega_2$), the luminescent light exiting from the object is measured on the difference frequency ($\Omega_1-\Omega_2$), and the luminescent light is analyzed as a function of the arithmetic mean ($\Omega$) of the modulation frequencies ($\Omega_1$; $\Omega_2$). The invention is applied in the semiconductor industry for determining different electrical parameters of semiconductor materials.

17 Claims, 11 Drawing Sheets

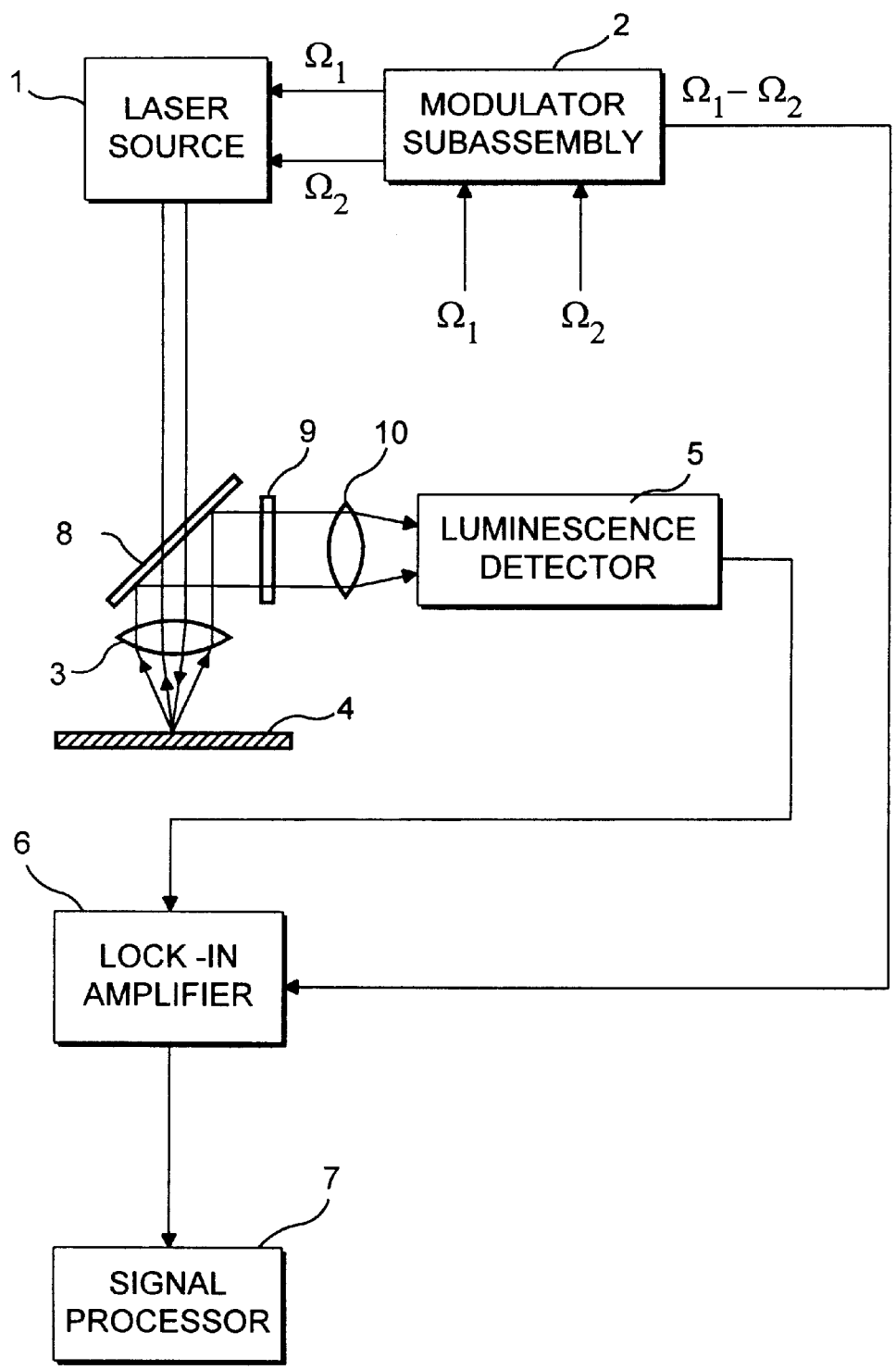
F I G. 2

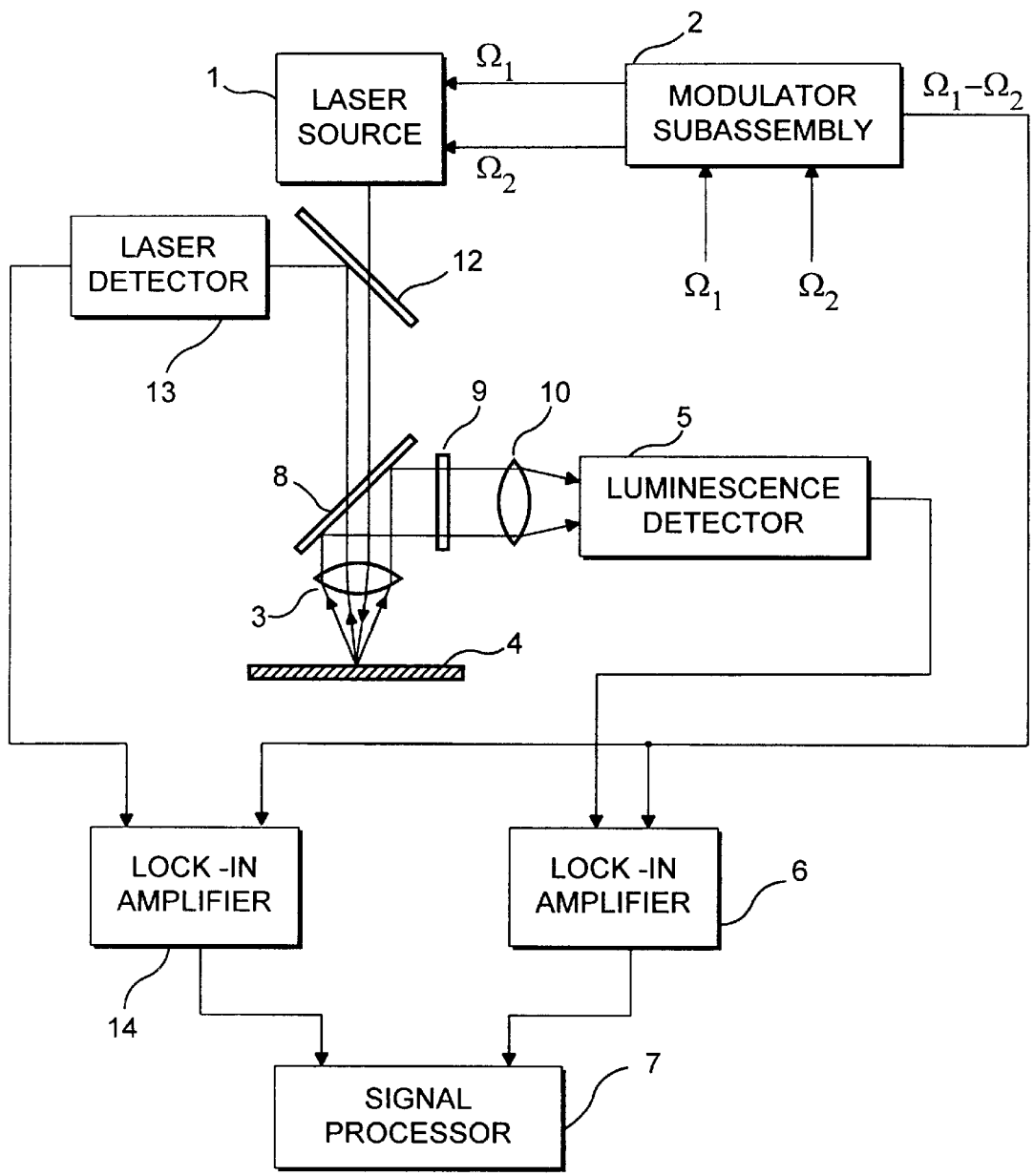
F I G. 4

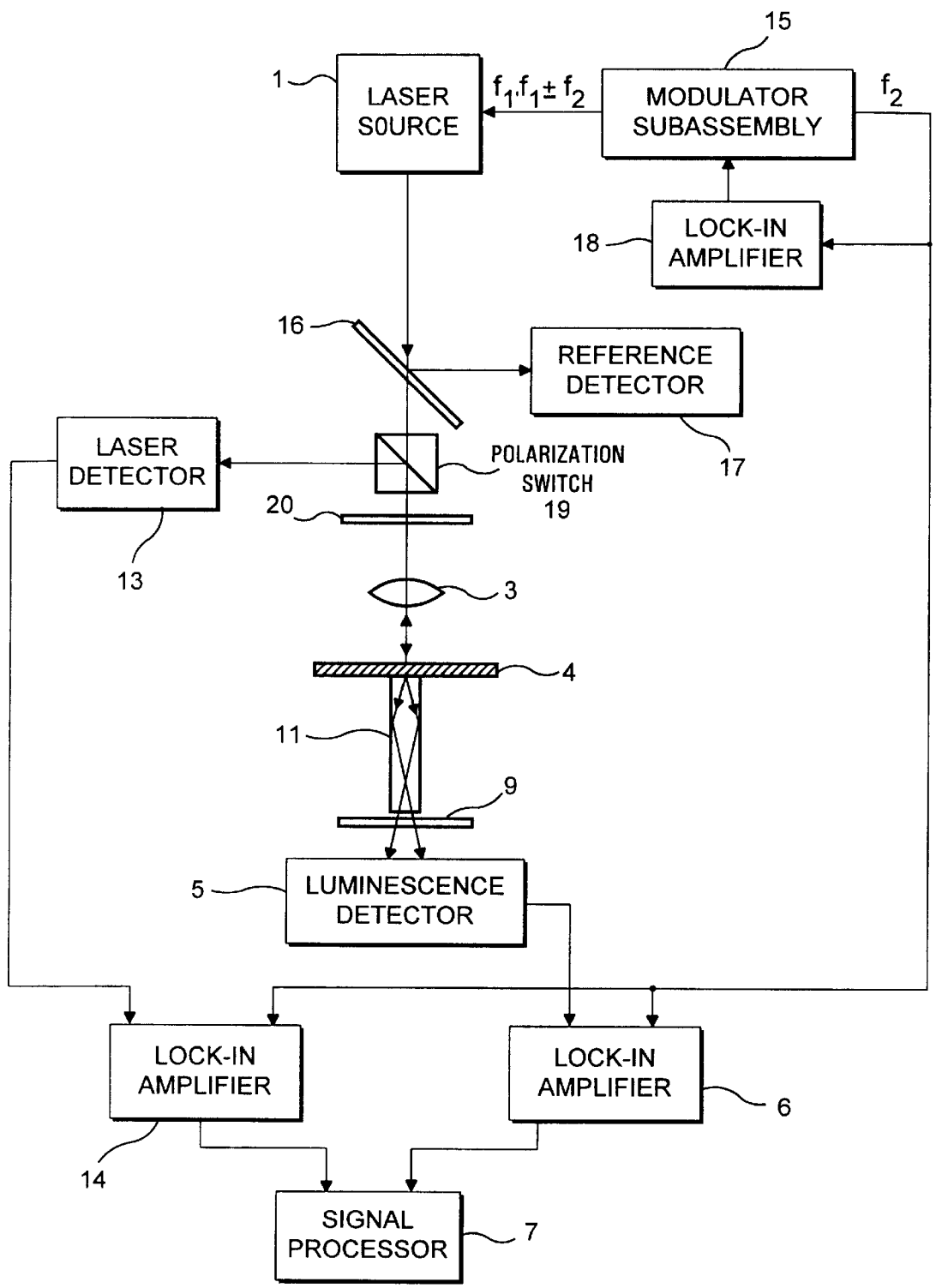
F I G. 5

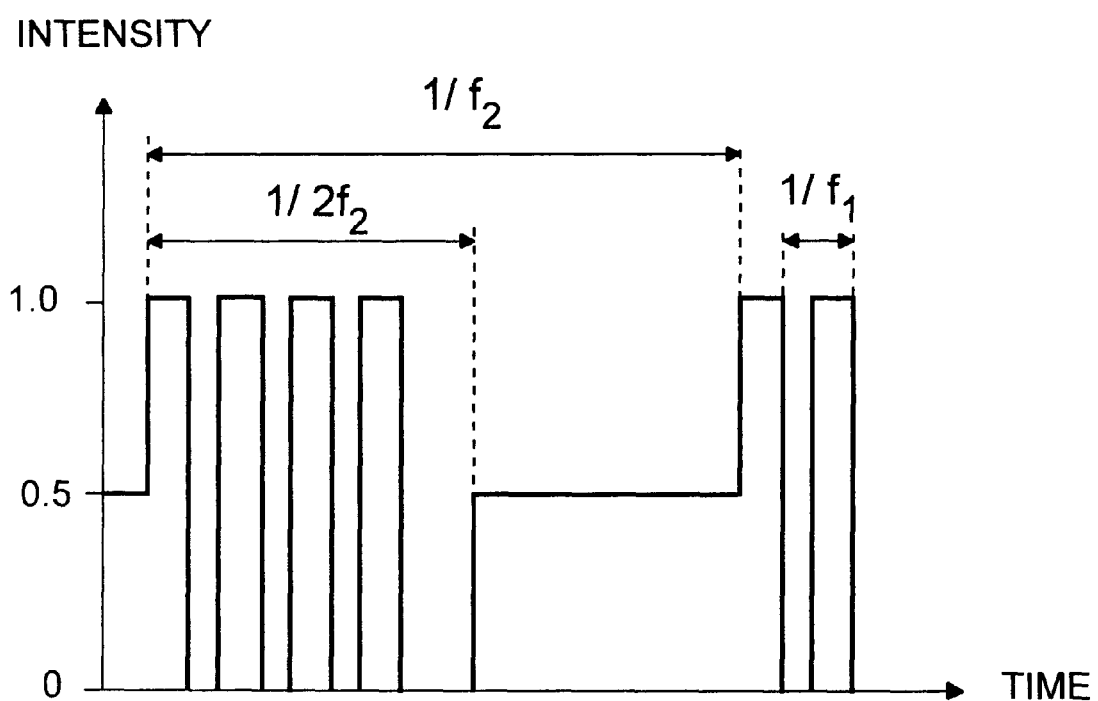
F I G. 6

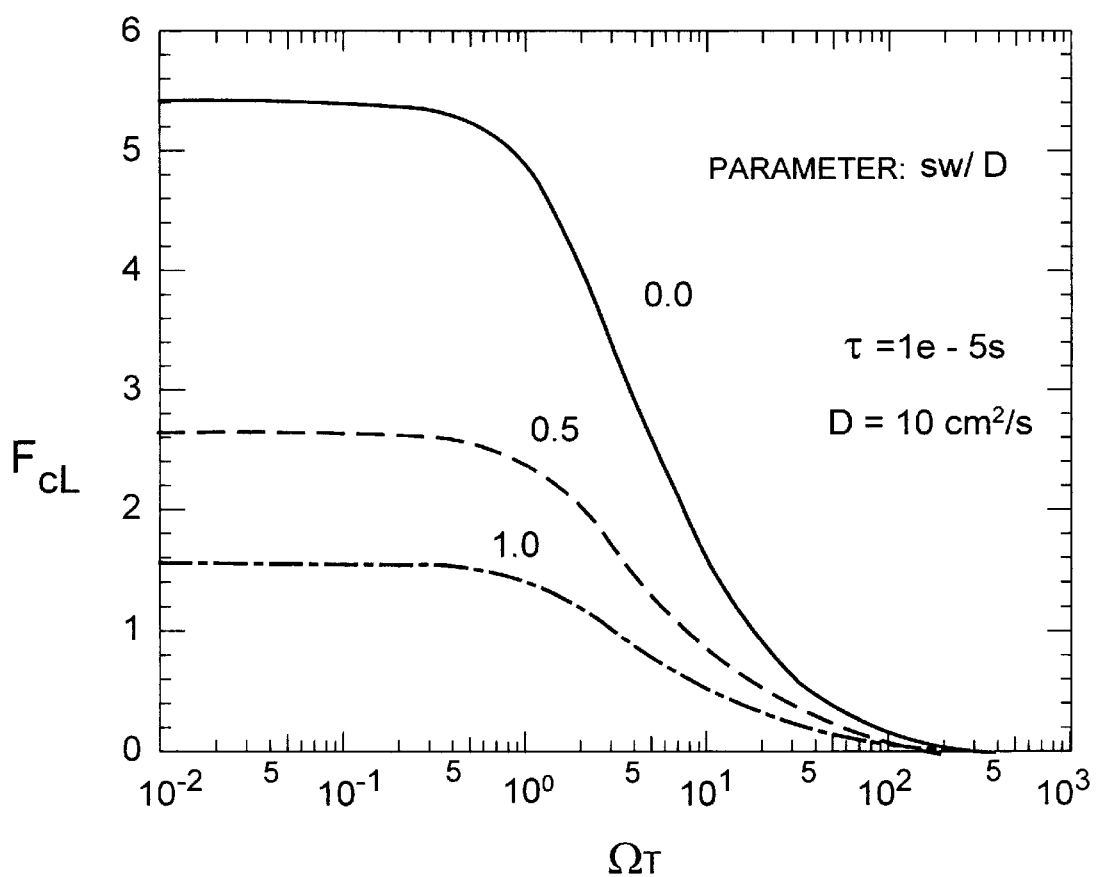
F I G.11

METHOD AND ARRANGEMENT FOR THE RESPONSE ANALYSIS OF SEMICONDUCTOR MATERIALS WITH OPTICAL EXCITATION

BACKGROUND OF THE INVENTION a) Field of the Invention

The invention is directed to a method and an arrangement for the response analysis of semiconductor materials with optical excitation, wherein an electronic energy deposit is effected in an object by means of a laser beam and its relaxation is measured in the form of luminescent radiation exiting from the specimen.

b) Description of the Related Art

In practice, the aim of conducting an analysis of the recombination channels in solids, chiefly in semiconductors, with a high local resolution as it applies to measuring technology is currently approached by means of contacting methods as well as noncontacting methods.

The fundamental drawback in the electrical or photoelectrical methods which use simple modulation with lock-in detection (in the case of frequency domains) or with boxcar integration (in the case of time domains) consists in the required contact. With regard to noncontacting methods, the measurement of photoluminescence is one of the oldest procedures for characterizing radiant recombination (e.g., see W. D. Johnston, Appl. Phys. Lett. 33 (1978) 992). A modulated excitation ensures the required measuring sensitivity and a high local resolution is made possible by the selection of the modulation frequency as can be gathered, e.g., from an article by J. Marek in Appl. Phys. Lett. 49 (1986) 1732. The locally resolved photoluminescence is generally generated with low excitation densities of the charge carrier wave by means of modulated laser radiation. In so doing, an intensity evaluation will be subject to substantial errors and, as a rule, only spectroscopy will be carried out. In addition, modulation is limited to low frequencies because of the simple separation of the direct-light component.

Further, various processes of photothermal spectroscopy with high excitation energy are known from the prior art as noncontacting methods, for which U.S. Pat. No. 4,579,463, DE 40 35 266, and DE 42 23 337 can be cited as representative sources. A problem in these processes is the dominance of the thermal wave, whereby the influence of the thermal characteristics of the material predominates in the measured parameters and the effect of the charge carrier wave approaches zero with charge carrier lifetimes of less than 1 µs. This drastically impairs the ability to determine electrical characteristics.

OBJECT AND SUMMARY OF THE INVENTION

Therefore, a primary object of the present invention is to find a new possibility for the response analysis of semiconductor materials with optical excitation which also allows a sufficiently precise detection of the charge carrier wave with a higher excitation output and a shorter charge carrier lifetime.

A further object of the invention is to detect radiating and nonradiating channels of the charge carrier recombination by means of optical excitation of the semiconductor and to make these channels capable of being evaluated individually.

In a method for the response analysis of semiconductor materials with optical excitation, in which an electronic energy deposit is carried out in an object by means of a laser beam and its relaxation is measured in the form of luminescent radiation exiting from the object, the object of the invention is met in that the exciting laser beam is intensity-modulated, wherein the frequency spectrum has two discrete modulation frequencies, in that the luminescent light exiting from the object is measured on a mixed frequency, namely either the sum frequency or the difference frequency of the modulation frequencies, and in that the luminescent light is analyzed as a function of the arithmetic mean of the modulation frequencies.

The two modulation frequencies are advantageously generated in the exciting laser beam in that the laser beam is formed of two partial beams, each partial beam being intensity-modulated with one of the modulation frequencies.

In order to graduate from simple luminescence mapping (the locally resolved luminescence measurement) to measurement values from which the electrical parameters of the semiconductor can be directly determined via model-based calculation, the modulation frequencies of the exciting laser beam are advisably varied within broad boundaries (frequency sweep), wherein the difference of the modulation frequencies is maintained constant.

The two partial beams are advantageously polarized at right angles to one another. Further, the two partial beams are advantageously focussed on spatially separated, closely adjacent points of incidence on the object for measuring the charge carrier lifetimes. For this purpose, the partial beams are advisably focussed on the object at a distance of at most twice the expected diffusion length of the excited charge carriers.

Another advantageous possibility for producing the two discrete modulation frequencies in the exciting laser beam is afforded by suitable amplitude modulation in that the laser beam is modulated with a carrier frequency $f_1 = (\Omega_1 + \Omega_2)/2$ and a base clock frequency $f_2 = \Omega_{1-2}$, and in that a component of the base clock frequency which is in phase with a mixed frequency resulting from the carrier frequency and the sidebands ($f_1 \pm f_2$) is detected and eliminated by feeding back this component to the modulation process as an interference quantity. In this variant of the double modulation of the exciting laser beam, as well, the two modulation frequencies are advisably varied within wide limits at a constantly maintained difference (frequency sweep) in order to enable the determination of electrical parameters of the object.

In general, there are three meaningful variants (regardless of the type of excitation) for detecting the luminescence radiation. A regularly advantageous variant, especially for semiconductor objects of considerable thickness, consists in detecting the luminescence on the excitation side of the object. Above all because of the automatically favorable shielding of the exciting laser beam, the luminescence is advisably recorded on the rear side of the object as determined with respect to the excitation. Certainly, the photoluminescence can also be advantageously measured on an optional lateral surface with respect to the excitation side of the object, e.g., at the circumferential surface of a semiconductor wafer.

For the purpose of solving the broadened problem at hand, in addition to the measurement of the luminescent light, a photothermal response is advantageously recorded from the laser beam after its interaction with the object and an analysis and correlation are carried out so that the nonradiating response of the object can be separated from the photothermal and luminescence response. The photothermal response is detected in a known manner, e.g., as described in DE 40 35 266 and DE 42 23 337.

In the combined simultaneous detection of the photoluminescence response and the photothermal response, the measured signals are advantageously recorded so as to be spatially separated in that the two measured values are detected on different sides of the object. Since the object is often poorly transparent to lasers, the photothermal response is advisably detected on the excitation side and the luminescence is recorded on the other side of the object (e.g., the rear side or lateral surface).

In an arrangement for the response analysis of semiconductor materials with optical excitation, in which a laser beam is focussed on an object to produce an electronic energy deposit and a luminescence detector is provided for measuring luminescent radiation exiting from the object, the object of the present invention is met in that the laser beam is intensity-modulated and contains two discrete modulation frequencies in a modulation spectrum, in that the luminescence detector is linked with a frequency-selective device, wherein only components of the luminescent radiation resulting from a frequency conversion taking place in the object are detectable on a mixed frequency, sum frequency or difference frequency of the modulation frequencies, and in that a signal processing device which analyzes the detector signals, which are detected in a frequency-selective manner, as a function of the arithmetic mean of the modulation frequencies is arranged downstream of the luminescence detector.

A laser source is advantageously used for generating the double-modulated laser beam and a modulator component group or subassembly is provided for modulating the laser source with the two modulation frequencies. Another advisable variant for generating the double-modulated laser beam consists in that the laser beam is formed of two partial beams, each partial beam being modulated with one of the modulation frequencies and the modulation being controlled by a modulator subassembly.

On the one hand, the two partial beams can be advantageously generated from a laser source by an optical divider, an optical modulator being arranged in each partial beam for modulation with one of the modulation frequencies, respectively, and optical means for bringing the partial beams together are arranged downstream of the modulators. Optical means for polarization are advisably provided in the partial beams so that the partial beams are polarized orthogonally to one another.

On the other hand, the partial beams can be advantageously generated in that two separate laser sources are provided, each laser source being driven with one of the modulation frequencies. In so doing, it proves advantageous to employ two laser diodes whose polarized light forms partial beams which are polarized at right angles to one another. In the simplest case, the partial beams generated in this way are guided into a common optical system so as to be parallel to one another and are focussed on a point on the surface of the object. The partial beams are advisably guided together so as to be coincident.

In a special arrangement, the partial beams are advantageously guided into the shared optical system in a nonparallel manner so that closely adjacent, spatially separated excitation centers of the partial beams are formed on the object. The diffusion length and mobility of the excited charge carriers can be determined in this way. In preparing the double-modulated laser beam, it is advantageous for purposes of calculating the electrical material parameters when a driving device is associated with the modulator subassembly, which driving device realizes a displacement of the modulation frequencies within wide limits (frequency sweep), wherein the arithmetic difference of the modulation frequencies always remains constant. The character of the radiating relaxation processes in the semiconductor can be determined from the frequency dependency of the luminescence intensity measurement.

In another construction of the arrangement according to the invention, a laser detector is advisably provided in addition to the luminescence detector for detecting the laser beam after its interaction with the object. This arrangement which is supplemented by the principles of thermal wave response detection known from DE 40 35 266 and DE 42 23 337 allows the luminescent signal component of the excited charge carriers to be separated from the total signal (supplied by the laser detector). This separation is based on the measurement of the photothermal response and the luminescent response, which are correlated with one another, over a broad modulation frequency range of the optical excitation of the object. The results provide information on the proportion of radiating and nonradiating channels in the semiconductor.

In order to prevent a corruption of the luminescence signal in the luminescence detector due to the exciting laser radiation, there are two advisable steps which are especially suitable for measuring reflected luminescence and for measuring transmitted luminescence. The laser light is separated by means of a dichroic mirror on the one hand and by an absorption filter on the other hand. The two steps can also be applied in combination or can be omitted if the object adequately shields the laser radiation.

The basic idea of the invention relies on knowledge of the luminescence as a radiating relaxation mechanism of charge carriers in semiconductors. This knowledge also applies analogously to all other possible radiating relaxation processes in a material.

Various methods of periodically modulated and nonperiodically modulated optical material excitation are known for the measurement of luminescence, e.g., from EP 0545523. On the other hand, excitation with a plurality of frequencies, two frequencies $\Omega_1$ and $\Omega_2$ in the simplest case, offers the advantage, with respect to measuring technique, of achieving a frequency conversion from the excitation frequency range to a favorable measurement frequency in terms of measuring technique by making use of the inherently nonlinear character of the excitation and relaxation processes. In the most elementary case where there is a quadratic dependence of the luminescence intensity on the excitation intensity, the luminescent radiation exiting the measurement object contains, in addition to the original frequencies of the excitation $\Omega_1$ and $\Omega_2$, their sum and difference frequencies $\Omega_1 \pm \Omega_2$. Accordingly, it is possible to carry out an analysis of the relaxation in a broad frequency range of excitation in a simple manner by detecting the components at the constant difference frequency $\Omega_1 - \Omega_2$ and, in so doing, also to advance into the range of high and ultra-high frequencies which can be accessed only with difficulty and with a loss in accuracy by means of the known methods. The character of the radiating relaxation processes, i.e., above all, their behavior with respect to time, can be determined from the frequency dependence of the intensity of the measured luminescent light.

In a first expansion of the basic idea of the invention, it is possible to obtain information concerning the diffusion length and mobility of the excited charge carriers in the object. A combination of two partial beams is used for excitation, each partial beam being intensity-modulated with one of the two frequencies $\Omega_1$ and $\Omega_2$ and guided through optical means in such a way that the partial beams strike the object at spatially separated points. The charge carrier concentration produced at the excitation centers is modulated either with frequency $\Omega_1$ or with frequency $\Omega_2$ in accordance with the impacting partial beam. In this case, luminescent light which is modulated with the difference frequency $\Omega_1-\Omega_2$ occurs only in the spatial region in which the concentrations of charge carriers modulated with $\Omega_1$ or $\Omega_2$ are superimposed. A sufficient superposition results when the relative distance between the excitation locations equals, at most, two diffusion lengths of the excited charge carriers. The variation in distance between the two points of incidence of the exciting laser beams therefore allows the dimensions of this spatial region to be determined in a simple manner by analyzing the dependence of the intensity of the luminescent light at difference frequency $\Omega_1-\Omega_2$ on the distance between the partial beams and their mean modulation frequency $(\Omega_1+\Omega_2)/2$.

In a second expansion of the inventive idea, the analysis of the radiating relaxation (photoluminescence) is combined with the analysis of the photothermal response signal.

It is known as a general problem in photothermal measurements, especially in semiconductors, that excited charge carriers contribute appreciably to the overall response of the object. By means of separate measurement of the radiation generated by the charge carrier recombination, it is possible to separate the signal component of the radiating relaxation of excited charge carriers from the overall signal. The separation is based on the measurement of the correlated photothermal response and luminescence signal of the object over a broad range of modulation frequencies of optical excitation. In this measurement process, the photothermal response analysis is likewise carried out on the basis of frequency conversion (photothermal heterodyning) as is described in Meas. Sci. Technol. 2 (1991) 1088–1093.

Contained in the portion of the excitation beam exiting the object are frequency-converted components which are marked by the interaction of nonradiating and radiating relaxation processes, while the frequency conversion in the luminescent light of the object proceeds exclusively from the radiating processes. Accordingly, it is possible to separate the response component of the radiating process by means of a correlated measurement of both response types and to obtain information on the nonradiating component.

By means of applying the basic variant of the method, according to the invention, luminescence measurements with a high resolution spatially and with respect to the signal-to-noise ratio can be obtained in a simple manner from the range of the band-to-band transition by radiating relaxation processes with high-frequency excitation and short charge carrier lifetimes (less than 1 $\mu$s). These measurements can also be effected in a reliable manner at high temperatures of the measured object (e.g., semiconductor substrates). Expanded variants of the method and corresponding special arrangements according to the invention make is possible to carry out a frequency analysis of the charge carrier wave, to obtain information concerning diffusion length and mobility of excited charge carriers, and to separate signal components of radiating and nonradiating response of the object in order to obtain information concerning luminescent and nonradiating channels in semiconductors and various electric material parameters.

The invention is explained more fully in the following with reference to embodiment examples.

BRIEF DESCRIPTION OF THE DRAWINGS

In the drawings:

FIG. 2 shows the basic construction, according to the invention, in a variant in which the luminescent light is detected on the excitation side of the object;

FIG. 4 shows another arrangement, according to the invention, for combined luminescence and photothermal spectroscopy with a frequency conversion in which the luminescent light is detected on the excitation side of the object;

FIG. 5 shows an arrangement, according to the invention, for combined luminescence and photothermal spectroscopy in which the excitation is effected by a laser beam with clocked modulation;

FIG. 6 shows the time curve of the intensity modulation for the embodiment variant described with reference to FIG. 5;

FIG. 11 shows the luminescence form function of FIG. 10 with a modified, normalized parameter.

DESCRIPTION OF THE PREFERRED EMBODIMENTS

In its basic variant, the method according to the invention comprises the introduction of energy into the object by means of intensity-modulated laser radiation with two discrete modulation frequencies $\Omega_1$ and $\Omega_2$, the detection of the luminescent light exiting from the object 4 at the sum frequency $(\Omega_1+\Omega_2)$ or difference frequency $(\Omega_1-\Omega_2)$, and the analysis of the detected luminescent light as a function of the arithmetic mean of the modulation frequencies.

Figure 1:
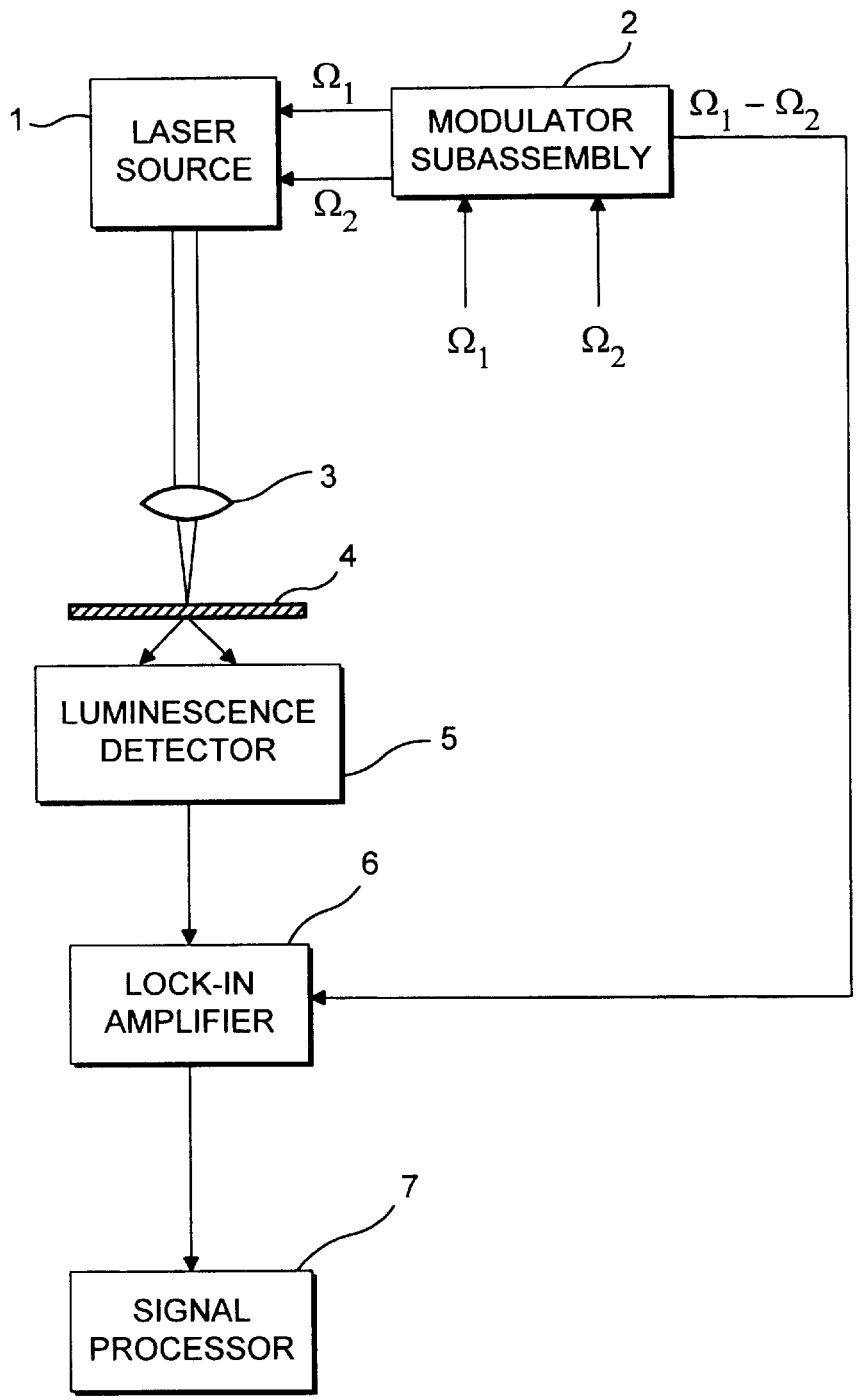
FIG. 1 shows the basic construction, according to the invention, in a variant in which the luminescent light is detected on the rear side of the object remote of the excitation.

The method is realized by means of an arrangement according to FIG. 1.

A laser beam is generated by a laser source 1 which is modulated in intensity with the two modulation frequencies $\Omega_1$ and $\Omega_2$ by means of a modulator subassembly 2. The modulation frequencies $\Omega_1$ and $\Omega_2$ can advantageously be fed in optionally in the frequency range of 100 kHz to 2 MHz and are generally selected so as to be relatively close together (e.g., $(\Omega_1-\Omega_2)\approx 10$ kHz). This matter is illustrated by the input arrows with $\Omega_1$ and $\Omega_2$ at the modulator subassembly 2. The laser beam is focussed by means of an optical system 3 and is guided to the object 4. The luminescent light exiting from the rear side of the object 4 is detected by a luminescence detector 5. Since the luminescent light does not exit in a collimated manner, this detector should detect the greatest possible spatial angle in order to minimize signal losses. For this reason, it is brought as close as possible to the rear side of the object 4. From the luminescence detector 5, the measurement signal proceeds to a lock-in amplifier 6 which is tuned to the difference frequency ($\Omega_1$-$\Omega_2$) and its reference signal is obtained from the modulator subassembly 2. Further signal processing is effected by a signal processor 7 which detects the output signal of the lock-in amplifier 6 and records and evaluates this signal as a function of $\Omega_1$ and $\Omega_2$.

In the arrangement according to FIG. 2, the laser beam is generated by the laser diode 1 which is intensity-modulated with the two modulation frequencies $\Omega_1$ and $\Omega_2$ by means of the modulator subassembly 2. The laser beam is guided onto the object 4 by a dichroic mirror 8 and the optical system 3. The dichroic mirror 8 is transparent for the wavelength of the laser light and has a comparatively high reflection factor for the luminescent light. The luminescent light exiting at the front side of the object 4 is collimated by the optical system 3, reflected at the dichroic mirror 8, and guided onto the luminescence detector 5 by optics 10. In the event that the dichroic mirror 8 is not sufficiently active for separating the laser light, an absorption filter 9 is added in the optical beam path. The measurement signal again proceeds from the luminescence detector 5 to the lock-in amplifier 6. Further signal processing is effected in accordance with the description in FIG. 1.

An expansion of the method according to the invention is achieved by carrying out a frequency sweep which can easily be realized without changes in the detection. The modulation frequencies $\Omega_1$ and $\Omega_2$ are varied over a broad frequency range, wherein it need only be ensured that the frequency difference ($\Omega_1$-$\Omega_2$) remains constant. The possibilities of evaluation of the measurement value are considerably expanded in this way, as will be shown hereinafter by way of theoretical considerations.

Another construction of the invention consists in combining the luminescent light detection with the recording of the photothermal response from the laser beam after its interaction with the object 4. Both response processes are recorded at the same time so that they are associated with the same location on the object 4. The evaluating mode is explained in the following.

The detection, according to the invention, of the luminescence response in the difference frequency or base clock frequency allows a frequency analysis of the charge carrier wave by varying the excitation frequency within the greatest possible interval which, however, covers the reciprocal of the charge carrier lifetimes τ in all cases. The signal S which represents a received luminescent light output can then be obtained by spatial integration of all luminescence components detected by the detector (ideally, the radiation is detected in a half-space HS):

$$S = LE_g\beta \int_{HS} d^3 \vec{r}\{n\cos(\Omega_1 t + \psi_n)p\cos(\Omega_2 t + \psi_p) + \quad (1)$$
$$n\cos(\Omega_2 t + \psi_n)p\cos(\Omega_1 + \psi_p)\}$$

The respective electron wave $n(\vec{r}; t)$ or hole wave $p(\vec{r}; t)$ is dependent, with respect to amplitude n or p (concentration of excess charge carriers in the band) and phase $\psi_n$ or $\psi_p$, on the location $\vec{r}$. The signal output is given, according to (1), by the luminescent light attenuation factor L, the mean energy of the luminescent light $E_g$, and the recombination rate $\beta = \sigma_L v$ in the luminescence channel. The latter is given by the capture cross section for radiating recombination $\sigma_L$ and the thermal velocity v of the charge carriers in the band and has the dimension [$m^3 s^{-1}$].

By carrying out a few transformations of the trigonometric functions in equation (1), the signal components S, which are determined only by the difference frequency $\Omega_{12}=\Omega_1-\Omega_2$, can be shown in the following form:

$$S = LE_g\beta\cos(\Omega_{12}t) \cdot \int_{HS} d^3 \vec{r}\{np\cos(\psi_n - \psi_p)\} \quad (2)$$
$$= LE_g\beta\cos(\Omega_{12}t) \cdot \int_{HS} d^3 \vec{r}\frac{1}{2}\{\hat{n}\cdot\hat{p}^* + \hat{n}^*\hat{p}\}$$

The term for the amount of a charge carrier wave (n,p) and the phase ($\psi_n$, $\psi_p$) has been replaced by the complex variables $\hat{c}=ce^{i\psi}$. (The complex conjugation is represented by *)

It will be appreciated that the phase information about the response wave cannot be separated and vanishes completely for excess charge carriers ($\psi_n \approx \psi_p$). However, it is still possible to extract the electrical material parameters, ambipolar diffusivity D, surface recombination velocity s, and excess charge carrier lifetime τ from $\hat{n}$ $\hat{p}$. In the ideal case of charge carrier waves (spherical waves), the integral can be calculated in a simple manner. Given a modulated laser output P deposited in an absorption zone determined by the laser spot radius w, the signal is determined according to the following equation:

$$S = L\cdot\frac{P^2 w}{(\hbar\omega D)^2}\frac{\beta\cdot E_g}{\left|1+\frac{ws}{D}+p\right|^2}\frac{1}{\{p+p^*\}}; \quad (3)$$

$$p^2 = (1+i\Omega\tau)\frac{w^2}{D\tau}$$

As will be seen, this scales with the laser spot radius w as a length measurement for the absolute measurement. It will be noted that the variable p defined in equation (3), as is generally customary, denotes the complex wave number of the charge carrier wave and may therefore not be confused with the concentration of excess holes p ($\vec{r}$, t). The following resulting variable with dimension [$W^{-1} m^{-1}$] is now introduced as conversion efficiency $K_L$ of the luminescence output at the difference frequency:

$$K_L = \frac{S}{P^2 w} = L\cdot\frac{\beta\cdot E_g}{(\hbar\omega D)^2}\cdot F_{cL} \quad (4)$$

The nondimensional luminescence form function $F_{cL}$ ($\Omega$) is determined by the mean modulation frequency $\Omega=(\Omega_1+\Omega_2)/2$ via the frequency sweep. The excess charge carrier lifetime τ is formed from luminescent ($\tau_L$) and nonradiating ($\tau_s$) channels according to the following equation:

$$1/\tau = 1/\tau_L + 1/\tau_s \quad (5)$$

Figure 10:
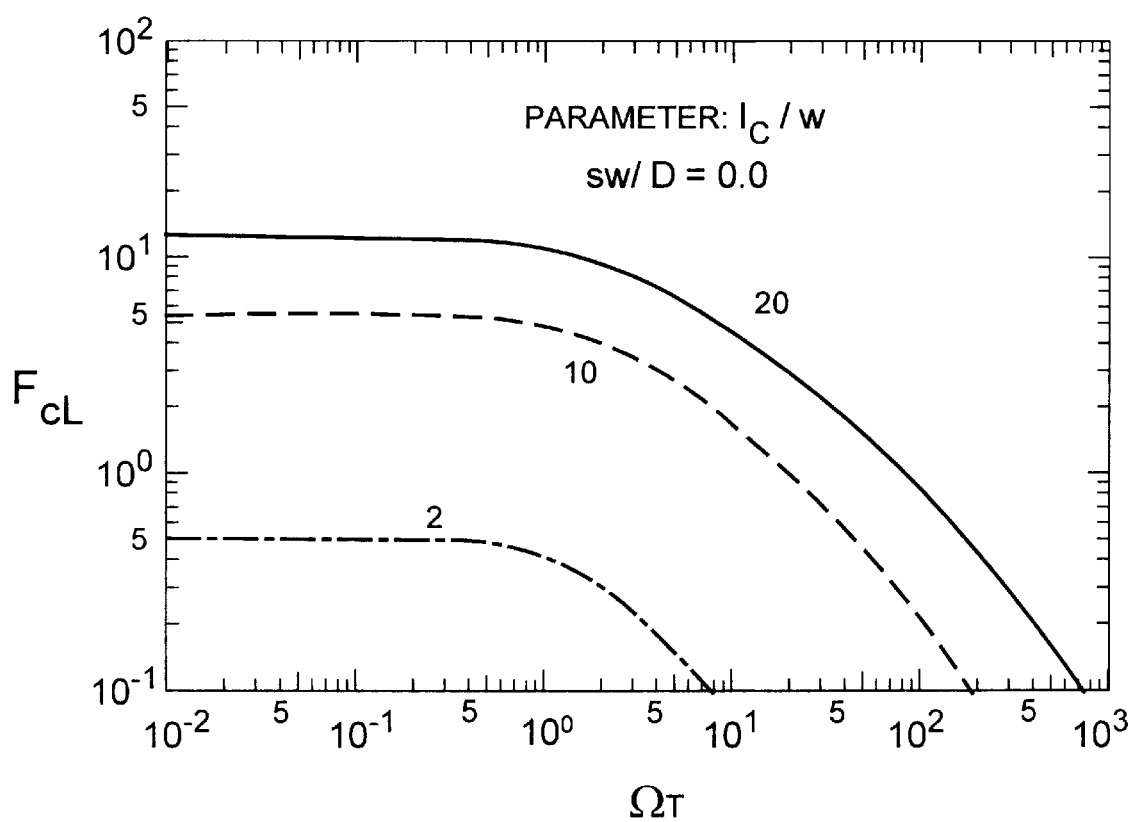
FIG. 10 shows the luminescence form function $F_{cL}$ dependent on the product of the mean modulation frequency $\Omega$ and mean lifetime $\tau$ of the excess charge carriers.

The form function is shown in FIGS. 10 and 11 for different dependencies. FIG. 10 shows the luminescence form function $F_{cL}$ over the product of the mean modulation frequency $\Omega$ and the mean lifetime τ of the excess charge carriers. The curve parameter is the charge carrier diffusion length $1_c = \sqrt{(2D\tau)}$ normalized to the laser spot radius w at a surface recombination velocity s =0.

FIG. 11 shows the luminescence form function $F_{cL}$ over the product of the mean modulation frequency $\Omega$ and the mean lifetime $\tau$ of the excess charge carriers. The curve parameter is the surface recombination velocity s normalized to the laser spot radius w and the diffusivity D at a fixed diffusion length $1_c$.

With respect to technical equipment, there are a number of variants for the combined evaluation of the luminescence response and photothermal response.

Figure 3:
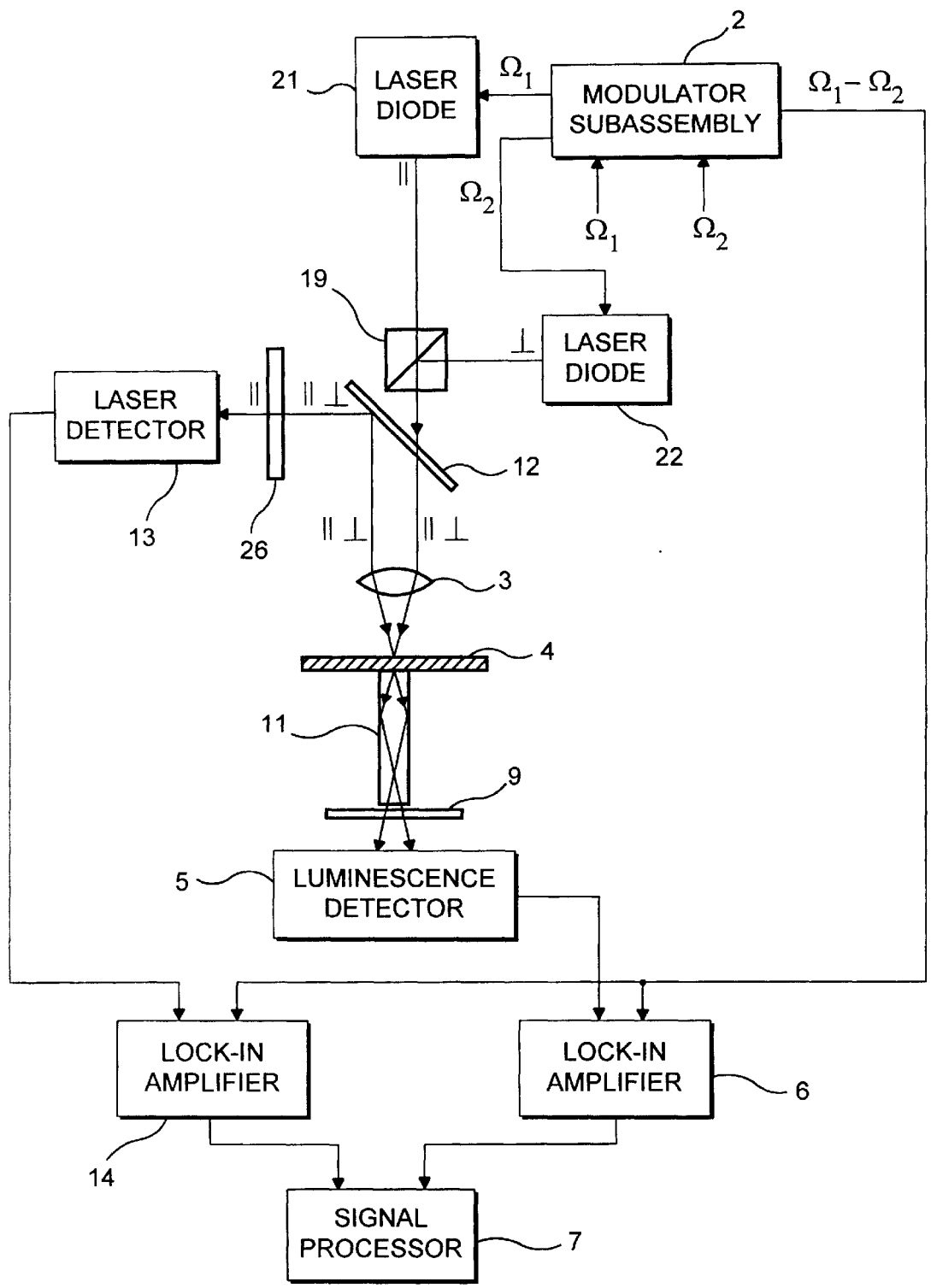
FIG. 3 shows an arrangement, according to the invention, for combined luminescence and photothermal spectroscopy with a frequency conversion in which the exciting laser beam is composed of two partial beams which are polarized so as to be directed vertically with respect to one another.

In the arrangement according to FIG. 3, the exciting laser beam is formed of two partial beams which are polarized ar right angles to one another and are generated by a laser diode 21 and another laser diode 22. Laser diode 21 is modulated in intensity by the modulator subassembly 2 with frequency $\Omega_1$ and laser diode 22 is modulated in intensity by the modulator subassembly 2 with frequency $\Omega_2$. The two partial beams are brought together via a polarization switch 19, pass through a divider plate 12, and are focussed on the object 4 by means of the optical system 3. In addition to the luminescent light exiting from the object 4, the laser beam is to be detected in this arrangement after its interaction with the object 4. The laser light exiting from the object 4 is collimated by the optical system 3 and, after being reflected at the divider plate 12, strikes a laser detector 13 which is suitable for this purpose. A polarization filter 26 is arranged upstream of this laser detector 13 and is oriented in such a way that only one of the two excitation partial beams returning from the object 4 is detected by the laser detector 13. The component of the laser light passing through the optical polarizing filter contains all of the information concerning the photothermal response by frequency conversion. When a different polarization filter 26 is selected (e.g., a polarization switch), this fact provides for the possibility of using the second laser light component for other purposes (e.g., reference detector, autofocus detector, etc.) without corruption of the response signals striking the laser detector 13.

Especially when lack of space prevents a positioning of the luminescence detector 5 directly on the object surface, the luminescent light exiting from the rear side of the object 4 is advantageously collected by means of a light guide 11 and is fed to the luminescence detector 5. In this embodiment form, a light guide 11 is used by way of example, since the luminescence detector 5 (regardless of its constructional shape) cannot always approach close enough to the rear of the object 4. For example, a glass rod which is polished on all sides or a glass-fiber bundle with a sufficient input cross section can be used as a light guide 11. A collimating optical system with a sufficiently high entrance aperture for detecting the sharply diverging luminescent light can also be used instead of the light guide 11. In the event that the object 4 has a noticeable or disturbing transparency for the wavelength of the exciting laser beam, the absorption filter 9 which is transparent to the luminescent light and absorbs the laser radiation is additionally introduced into the beam path. The measurement signals proceed from the luminescence detector 5 and from the laser detector 13 to the lock-in amplifier 6, which was already described, and to an additional lock-in amplifier 14 which analyzes the amplitude and phase of the signal supplied by the laser detector 13. The two lock-in amplifiers 6 and 14 are tuned to the difference frequency $(\Omega_1-\Omega_2)$ and obtain their reference signal from the modulator subassembly 2. Their output signals are fed to the signal processor 7 which also brings about a correlation of the measurement signals supplied from the lock-in amplifiers 6 and 14 by way of the recording and evaluation of the measurement signals, mentioned above, by means of the excitation frequency. The processor supplies separate information for radiating and nonradiating relaxation mechanisms in the object by applying algorithms of a suitable theoretical model, mentioned above. A microcomputer system, for example, can serve as a signal processor for an extensive signal analysis of this kind.

In the arrangement according to FIG. 4, the laser beam is generated by the laser diode 1 which is intensity-modulated with the two modulation frequencies $\Omega_1$ and $\Omega_2$ by means of the modulator subassembly 2. The laser beam traverses a divider plate 12 and the dichroic mirror 8 and is guided to the object 4 by means of the optical system 3. The laser light which exits again from the object 4 is detected and collimated by the optical system 3, passes through the dichroic mirror 8 and, after being reflected at the divider plate 12, strikes a laser detector 13 which is suitable for this purpose. The luminescent light exiting at the front side of the object 4 is collimated by the optical system 3, reflected at the dichroic mirror 8, and guided to the luminescence detector 5 by optics 10. If the dichroic mirror 8 is not sufficiently active for separating the laser light, an absorption filter 9 is included in the beam path. The measurement signal proceeds from the luminescence detector 5 to the lock-in amplifier 6 and from the laser detector 13 to the lock-in amplifier 14. Further signal processing is effected corresponding to the description referring to FIG. 3.

In the arrangement according to FIG. 5, the exciting laser beam is generated by the laser diode 1 which is intensity-modulated by a modulator subassembly 15. The intensity curve of the laser beam generated by this modulator subassembly 15 is shown over time in FIG. 6. A component is coupled out of the laser beam via a beam splitter 16 and is directed to an optical reference detector 17. This reference detector 17, together with a lock-in amplifier 18 and the modulator subassembly 15, forms a control loop. This control loop causes the component detected in the exciting laser beam by the reference detector 17 to be regulated to zero at frequency $f_2$. This type of modulation is described in DE 42 23 337. The exciting laser beam is guided to the object 4 by the optical system 3 after passing the polarization switch 19 and a $\lambda/4$-plate 20. The portion of the laser beam which exits the object 4 again is detected by the optical system 3, passes through the $\lambda/4$-plate 20 again, and is coupled out at the polarization switch 19 to the laser detector 13. The luminescent light is collected from the rear side of the object 4 by means of the light guide 11 and is directed to the luminescence detector 5. The absorption filter 9 can be introduced into the beam path again in order to separate disturbing components of the exciting laser light which are transmitted by the object 4. The signals proceed from the luminescence detector 5 and from the laser detector 13 to the lock-in amplifiers 6 and 14 which are tuned to the base clock frequency $f_2$ and which obtain their reference signal from the modulator subassembly 15. Further signal processing is effected by the signal processor 7 according to the description with reference to FIG. 3.

In all of the preceding variants, the luminescent light and the laser beam were analyzed after interacting with the object 4 at the difference frequency $(\Omega_1-\Omega_2)$ corresponding to claim 1. This embodiment form is particularly advantageous because an analysis can be conducted in a simple manner over a broad frequency range by tuning the two modulation frequencies $\Omega_1$ and $\Omega_2$ in the same direction at a frequency separation which is maintained constant. However, it can sometimes be disadvantageous that no phase information of the response can be obtained from the detected luminescent light. In order to obtain the phase information, the analysis is advisably carried out at the sum frequency $(\Omega_1+\Omega_2)$. This type of operation is particularly advantageous with respect to the arrangements shown in FIG. 7 and FIG. 8, although the invention is not limited by these special arrangements.

Figure 7:
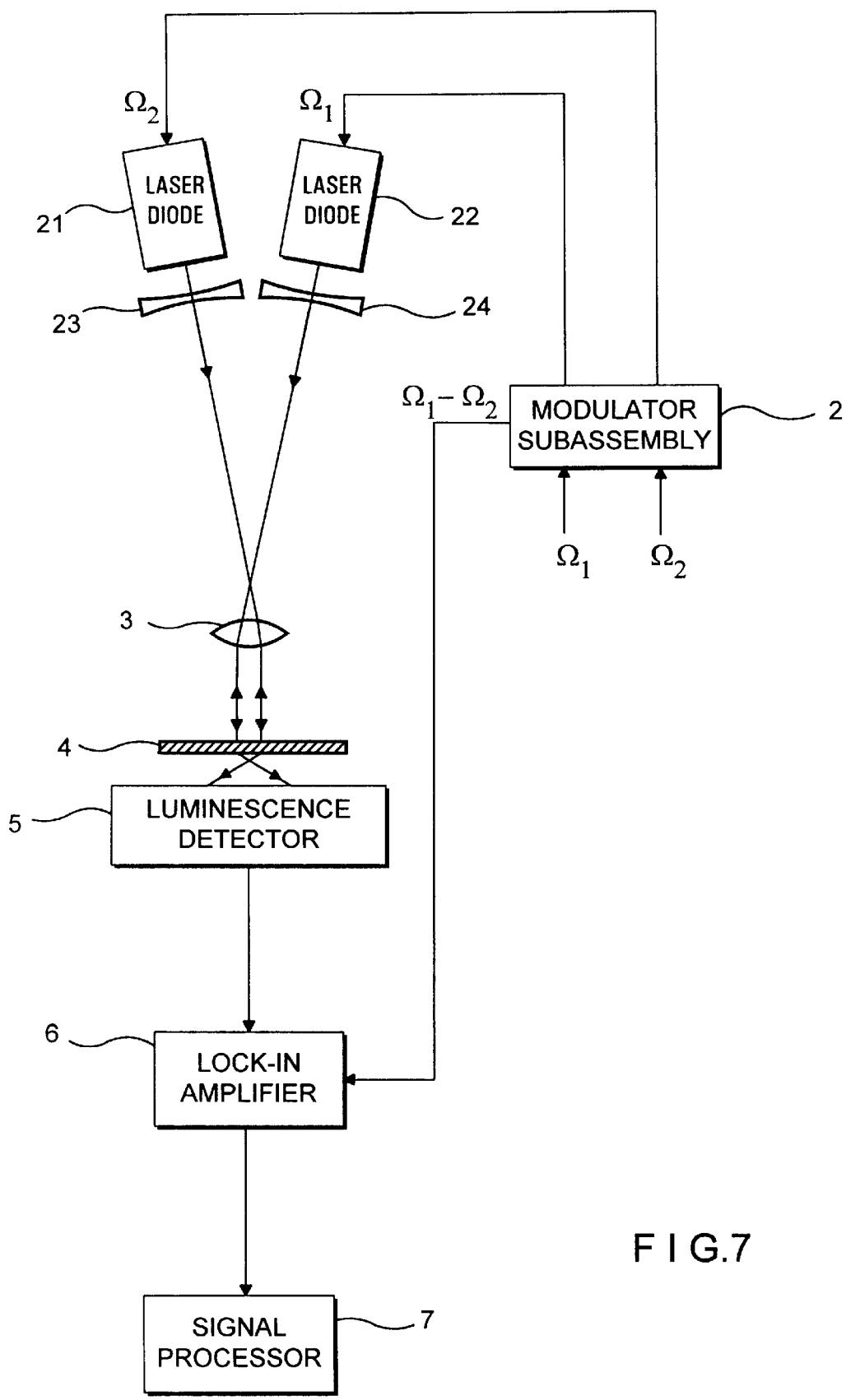
FIG. 7 shows an arrangement, according to the invention, with two partial beams which excite the object in spatially separated excitation centers.

In the arrangement according to FIG. 7, two laser beams are generated by two laser diodes 21 and 22 whose intensities are modulated by means of the modulator subassembly 2 with one of the modulation frequencies $\Omega_1$ and $\Omega_2$, respectively. Both laser beams enter the optical system 3 and are focussed on the object 4 as spatially separated exciting partial beams. The distance between the points of incidence can be varied by changing the angle of inclination of the partial beams by means of two sliding lenses 23 and 24. The luminescent light exiting from the rear of the object 4 is detected by the luminescence detector 5. The measurement signal proceeds from the luminescence detector 5 to the lock-in amplifier 6 which is tuned to the difference frequency $(\Omega_1-\Omega_2)$ and obtains its reference signal from the modulator subassembly 2. Further signal processing is effected by the signal processor 7 which detects the output signal of the lock-in amplifier 6 and records and evaluates this signal as a function of $\Omega_1$ and $\Omega_2$ and depending upon the spatial distance of the points of incidence of the partial beams.

The type of frequency-selective recording of the measurement value at the sum frequency $\Omega_1+\Omega_2$ of the modulation frequencies $\Omega_1$ and $\Omega_2$, which likewise belongs to the essence of the invention, can be carried out advantageously in this constructional variant (as well as in the arrangement according to FIG. 8 which is described hereinafter) in that the luminescent light is analyzed at fixed modulation frequencies $\Omega_1$ and $\Omega_2$ as a function of the relative distance of the points of incidence of the exciting partial beams.

Figure 8:
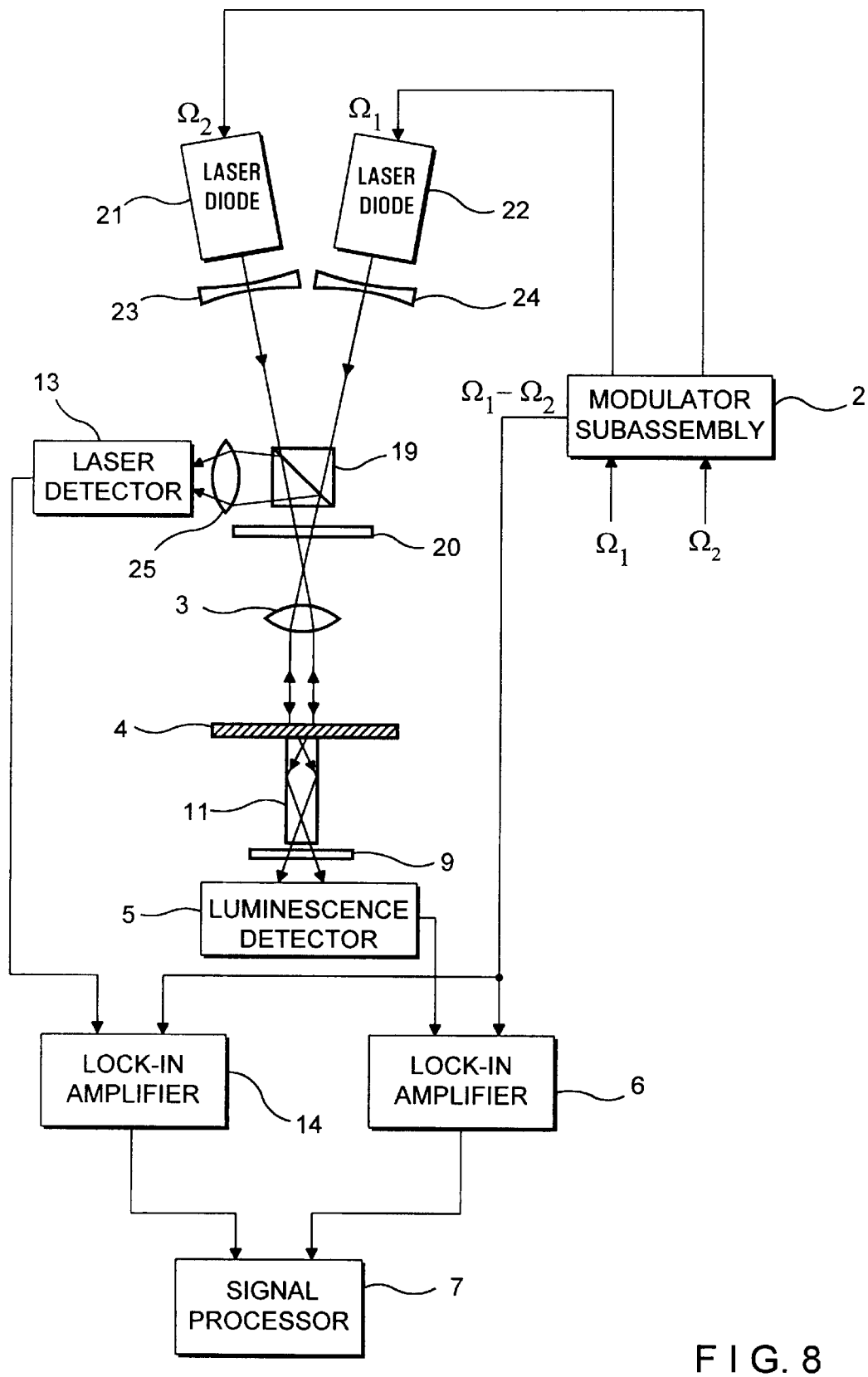
FIG. 8 shows another arrangement, according to the invention, with two spatially separated exciting partial beams.

In the arrangement according to FIG. 8, two laser beams are generated by two laser diodes 21 and 22 whose intensities are modulated with one of the frequencies $(\Omega_1$ and $\Omega_2)$, respectively. The signals for the intensity modulation are prepared by the modulator subassembly 2. Both laser beams pass through the polarization switch 19 and the λ/4-plate 20, enter the optical system 3, and are focussed on the object 4 as spatially separated exciting partial beams. The distance between the points of incidence can be varied by changing the angle of incidence of the partial beams by means of the two sliding lenses 23 and 24. The proportion of the excitation beams exiting the object again is detected by the optical system 3, passes through the λ/4-plate again, is coupled out at the polarization switch 19, and is guided to the laser detector 13 by means of a lens 25. The luminescent light exiting from the rear of the object is detected by the light guide 11 and is guided to the luminescence detector 5. In the event of a disruptive transmission of components of the exciting laser light through the object 4, the absorption filter 9 can be introduced into the beam path again. The measurement signal proceeds from the luminescence detector 5 to the lock-in amplifier 6 which is tuned to the difference frequency $(\Omega_1-\Omega_2)$ and obtains its reference signal from the modulator subassembly 2. Further signal processing is effected by the signal processor 7 which detects the output signal of the lock-in amplifier 6 and records and evaluates this signal as a function of $\Omega_1$ and $\Omega_2$ and depending upon the spatial distance of the points of incidence of the partial beams and, beyond this, carries out the correlated analysis of the signals supplied by the detectors 5 and 13 according to the embodiment example shown in FIG. 3.

Figure 9:
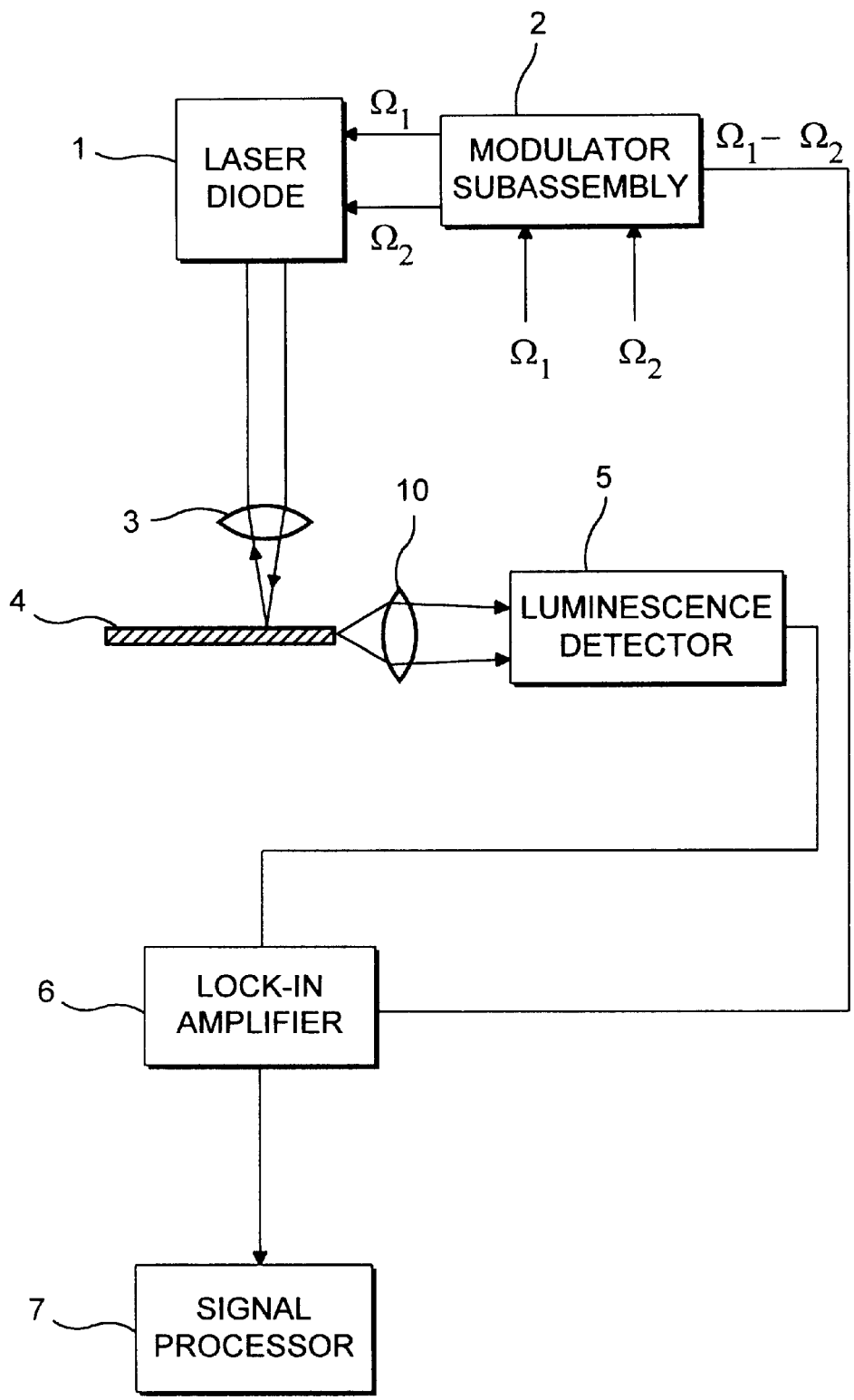
FIG. 9 shows an arrangement, according to the invention, with lateral detection of the luminescent light.

FIG. 9 shows a modification of the basic arrangement shown in FIG. 1. This modified arrangement can be applied for analyzing objects in which a comparatively high proportion of the luminescent light exits laterally from the object 4 and can be picked up easily at this location by the luminescence detector 5. This is often the case, e.g., in the analysis of polished semiconductor wafers in which a comparatively high proportion of the luminescent light can propagate in the material by light conduction. In the arrangement according to FIG. 9, the laser beam is generated by the laser diode 1 which is intensity-modulated by the modulator subassembly 2 with the two frequencies $\Omega_1$ and $\Omega_2$. The laser beam is focussed by means of the optical system 3 and is guided to the object 4. The luminescent light exiting laterally from the object 4 is collected by the lens 10 and fed to the luminescence detector 5. The measurement signal proceeds from the luminescence detector 5 to a lock-in amplifier 6 which is tuned to the difference frequency $(\Omega_1-\Omega_2)$ and which obtains its reference signal from the modulator subassembly 2. Further signal processing is effected by the signal processor 7 which detects the output signal of the lock-in amplifier 6 and records and evaluates this signal as a function of $\Omega_1$ and $\Omega_2$.

Of course, the detection of the luminescent light exiting laterally from the object 4 which is illustrated in FIG. 9 can also be applied in all other modifications of the basic arrangement according to the invention which are described with reference to FIGS. 2 to 8.

While the foregoing description and drawings represent the preferred embodiments of the present invention, it will be obvious to those skilled in the art that various changes and modifications may be made therein without departing from the true spirit and scope of the present invention.

What is claimed is:

1. In an arrangement for the response analysis of semiconductor materials with optical excitation, in which a double-modulated laser beam of a laser source is focussed on an object for the purpose of an electronic energy deposit the relaxation of which is measured in the form of an intensity of luminescent radiation exiting from the object by means of a luminescence detector, the improvement comprising:

means for intensity-modulating the laser beam with two discrete modulation frequencies $(\Omega_1; \Omega_2)$;

a frequency-selective device linked with said luminance detector so that only components of the luminescent radiation resulting from a frequency conversion taking place in the object are detectable on a constant difference frequency $(\Omega_1-\Omega_2)$ of the modulation frequencies $(\Omega_1; \Omega_2)$; the modulation frequencies $(\Omega_1; \Omega_2)$ being in the range from 100 kHz to 2 MHz and the difference frequency $(\Omega_1-\Omega_2)$ being in an order of 10 KHz; and a signal processing device arranged downstream of the luminescence detector for analyzing the detected components of the luminescence radiation as a function of the arithmetic mean $((\Omega_1+\Omega_2/2))$ of the modulation frequencies $(\Omega_1; \Omega_2)$.

2. The arrangement according to claim 1, wherein said laser beam intensity modulating means includes a laser source for generating the double-modulated laser beam and a modulator subassembly for modulating the laser source with the two modulation frequencies $(\Omega_1; \Omega_2)$.

3. The arrangement according to claim 1, wherein the laser beam is formed of two partial beams, each partial beam being modulated with one of the modulation frequencies $(\Omega_1; \Omega_2)$ and the modulation being controlled by a modulator subassembly.

4. The arrangement according to claim 3, wherein a laser source follows an optical divider for the purpose of generating two partial beams, wherein an optical modulator is arranged in each partial beam for modulation with one of the modulation frequencies ($\Omega_1$; $\Omega_2$), respectively, and optical means are provided for bringing the partial beams together are arranged downstream of the modulators.

5. The arrangement according to claim 4, wherein optical means for polarization are provided in the partial beams so that the partial beams are polarized at right angles to one another.

6. The arrangement according to claim 3, wherein there are two separate laser sources which are connected with a modulator subassembly, each laser source being driven with one of the modulation frequencies ($\Omega_1$; $\Omega_2$).

7. The arrangement according to claim 6, wherein two laser diodes serve as laser sources and are adjusted in such a way that their polarized light forms partial beams which are polarized at right angles to one another.

8. The arrangement according to claim 7, including means for guiding the partial beams into a common optical system so as to be parallel to one another and to be focussed on a point on the surface of the object.

9. The arrangement according to claim 7, including means for bringing the partial beams together so as to be coincident.

10. The arrangement according to claim 7, including means for guiding the partial beams into the common optical system in a nonparallel manner so that closely adjacent, spatially separated points of incidence of the partial beams are formed on the object.

11. The arrangement according to claim 10, wherein the points of incidence are separated by a distance amounting to, at most, twice the expected diffusion length of the excited charge carriers.

12. The arrangement according to claim 10, including means for adjusting the frequency-selective device in such a way that only components of the luminescent radiation resulting from a frequency conversion taking place in the object are detectable on the sum frequency ($\Omega_1+\Omega_2$) of the modulation frequencies ($\Omega_1$; $\Omega_2$) for the purpose of detecting the difference frequency ($\Omega_1-\Omega_2$).

13. The arrangement according to claim 1, wherein a driving device is provided for displacement of the modulation frequencies ($\Omega_1$; $\Omega_2$) within wide limits, wherein the driving device is connected with the modulator subassembly and the arithmetic difference of the modulation frequencies ($\Omega_1$; $\Omega_2$) always remains constant.

14. The arrangement according to claim 1, wherein a laser detector is provided in addition to the luminescence detector for detecting the laser beam after its interaction with the object.

15. The arrangement according to claim 14, including means for guiding the outputs of the luminescence detector and laser detector to a lock-in amplifier in each instance, wherein the two lock-in amplifiers, as frequency-selective devices, are tuned to the difference frequency ($\Omega_1-\Omega_2$) of the modulation frequencies ($\Omega_1$; $\Omega_2$) and are connected with the modulator subassembly for supplying reference signals, and the signal processing device is a signal processor for recording, evaluating, and correlating the output signals of the two lock-in amplifiers and supplies separate information concerning radiating and nonradiating relaxation processes in the object.

16. The arrangement according to claim 1, wherein a dichroic mirror is provided for separating the laser light from the luminescent radiation.

17. The arrangement according to claim 1, wherein an absorption filter is arranged upstream of the luminescence detector for separating the interfering laser light from the luminescent radiation.

| List of Reference Numbers | |
|---|---|
| 1 | laser source |
| 2 | modulator subassembly |
| 3 | optical system |
| 4 | object |
| 5 | luminescence detector |
| 6 | lock-in amplifier |
| 7 | signal processor |
| 8 | dichroic mirror |
| 9 | absorption filter |
| 10 | optics |
| 11 | light guide |
| 13 | laser detector |
| 14 | lock-in amplifier |
| 15 | modulator subassembly |
| 16 | beam divider |
| 17 | reference detector |
| 18 | lock-in amplifier |
| 19 | polarization switch |
| 20 | $\lambda$/4-plate |
| 21, 22 | laser diode |
| 23, 24 | sliding lenses |
| 25 | lens |
| 26 | polarization filter |
| D | diffusivity |
| $F_{cL}$ | luminescence form function |
| $l_c$ | diffusion length |
| s | surface recombination velocity |
| w | laser spot radius |
| $\tau$ | lifetime |
| $\Omega$ | arithmetic mean of the modulation frequencies |
| ($\Omega_1$, $\Omega_2$) | modulation frequencies |
| ($\Omega_1 + \Omega_2$) | sum frequency |
| ($\Omega_1 - \Omega_2$) | difference frequency |

* * * * *